United States Patent [19]

Emmrich et al.

[11] Patent Number: 5,080,761
[45] Date of Patent: Jan. 14, 1992

[54] METHOD OF OPTIMIZING THE OPERATION OF A DISTILLATION COLUMN PROVIDED WITH A SIDE HEATING DEVICE

[75] Inventors: Gerd Emmrich, Essen; Hans-Christoph Schneider, Hattingen; Ulrich Rüdel, Oberhausen, all of Fed. Rep. of Germany

[73] Assignee: Krupp Koppers GmbH, Essen, Fed. Rep. of Germany

[21] Appl. No.: 403,143

[22] Filed: Sep. 1, 1989

[30] Foreign Application Priority Data

Sep. 23, 1988 [DE] Fed. Rep. of Germany ....... 3832340

[51] Int. Cl.$^5$ .............................................. B01D 3/14
[52] U.S. Cl. ...................................... 203/98; 203/58; 203/DIG. 9; 203/DIG. 19; 202/156
[58] Field of Search ............... 203/58, 50, 98, 94, 203/DIG. 19, 99, DIG. 9; 202/156, 153, 158; 585/860

[56] References Cited

U.S. PATENT DOCUMENTS

| | | | |
|---|---|---|---|
| 3,080,300 | 3/1963 | Smith | 203/88 |
| 3,349,010 | 10/1967 | Plaster | 203/DIG. 9 |
| 3,412,016 | 11/1968 | Graven | 203/98 |
| 4,230,533 | 10/1980 | Giroux | 203/98 |
| 4,247,368 | 1/1981 | Bannon et al. | 203/98 |
| 4,349,416 | 9/1982 | Brandt et al. | 203/98 |
| 4,410,400 | 10/1983 | Preusser et al. | 203/98 |
| 4,655,879 | 4/1987 | Brockman et al. | 203/98 |
| 4,661,208 | 4/1987 | Honma et al. | 203/98 |
| 4,725,338 | 2/1988 | Asanuma et al. | 203/98 |

Primary Examiner—Wilbur Bascomb
Attorney, Agent, or Firm—Michael J. Striker

[57] ABSTRACT

In a method of optimizing the operation of a distillation column with a side heating device for reconditioning of extract which is received during the extraction of hydrocarbon-containing initial products with N-substituted morpholines whose substituents have not more than seven C-atoms as selective solvents a liquid is withdrawn to a side heating device through a chimney plate arranged above a feed plate, so that between 5 and 30 volume percent of the liquid supplied to the chimney plate is not withdrawn to the side heating device but instead supplied directly to a plate located underneath the chimney plate. A vapor-liquid mixture which has escaped through a top from the side heating device is returned back to the distillation column. The returned vapor-liquid mixture is fed either to the feed plate or to the plate located underneath the chimney plate. An arrangement for performing the inventive method is also provided.

3 Claims, 3 Drawing Sheets

METHOD OF OPTIMIZING THE OPERATION OF A DISTILLATION COLUMN PROVIDED WITH A SIDE HEATING DEVICE

BACKGROUND OF THE INVENTION

The present invention relates to a method of and an arrangement for optimizing the operation of a distillation column provided with a side heating device, for reconditioning of the extract which is received during the extraction of hydrocarbon-containing starting materials with N-substituted morpholines whose substituents have no more than seven C atoms as selective solvents.

The extraction of hydrocarbon containing starting products with the above-mentioned N-substituted morpholines especially with N-formyl morpholines as selective solvents has been known for a long time and is used nowadays on large scale, first of all for recovery of aromates of high purity. The method is also suitable for recovery of other classes of materials, for example olefin and diolefin, whereas both the extracted distillation as well as liquid-liquid extraction can be utilized. The hydrocarbon to be recovered from the respective starting products concentrates together with the main quantity of the solvent in the extract and must be separated from the solvent in the distillation column located after the extraction stage. The hydrocarbon to be recovered is distilled through the top from the distillation column, while the solvent precipitates as sump product of the column and can be supplied from there for a further utilization. The distillation column can be provided for its heating in addition to the conventional sump circulating heating device, also with a side heating device which first of all must evaporate the return flow from the distillation column.

During operation of such distillation columns especially in connection with the utilization of N-formyl morpholine as selected solvent, it has been determined that the solvent is concentrated on the plate of the distillation column, which lies above the outlet of the heating device and simultaneously is a withdrawing plate for the side heating device. Thereby the boiling temperature on this plate is increased and therefore the heat output of the plate is continuously worsened. By an increase of the return flow the heat discharge of the side heating device can be increased. This, however brings no advantage, since the sump circulating heating device of the distillation column must supply the same quantity of heat and thereby its total thermal balance is not improved.

SUMMARY OF THE INVENTION

Accordingly, it is an object of the present invention to provide a stabilization of the operation of the distillation column in such a manner that the above-described disadvantages are eliminated and the operation of the side heating device can be considerably improved.

In keeping with these objects and with others which will become apparent hereinafter, one feature of the present invention resides, briefly stated, in a distillation column of the above mentioned type in which the liquid withdrawal to a side heating device is performed through a chimney plate arranged above the feed plate and between 5-30 volume percent of the liquid supplied to the chimney plate is not withdrawn in the side heating device but instead supplied directly to the plate located underneath, and the vapor-liquid mixture discharging over the top from the side heating device is supplied back into the distillation column so that it is fed either on the feed plate or on the plate located under the chimney plate.

In accordance with another feature of the present invention an arrangement is proposed in which a chimney plate provided with an overflow weir is arranged in the distillation column above the feed plate, the total length of the overflow weir is subdivided into two portions, behind which a discharge cup for withdrawing the liquid to the side heating device and a discharge passage leading to the lower plate are located, and the subdivision into two portions corresponds to the desired subdivision of two liquid partial streams withdrawn from the chimney plate.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
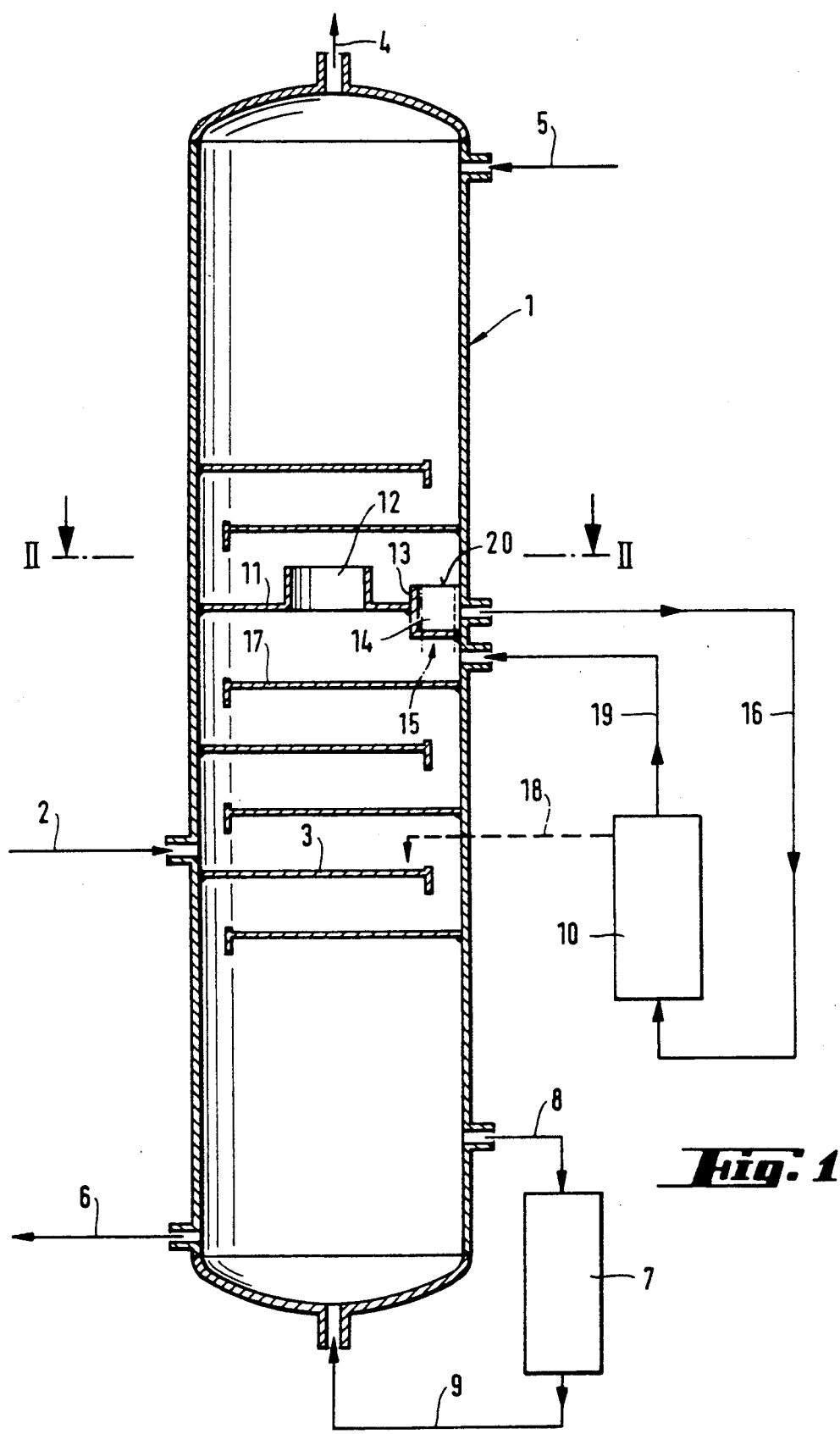
FIG. 1 is a view schematically showing a distillation column 34 for the inventive method.

In accordance with the present invention a method is proposed in which the withdrawal of liquid as a side flow from the distillation column to a side heating device is performed through a chimney plate arranged above the feed plate and between 5-30 volume percent of the liquid supplied to the chimney plate is not withdrawn in the side heating device but instead supplied directly to the plate located underneath, and the vapor-liquid mixture discharging over the top from the side heating device is supplied back into the distillation column so that it is fed either on the feed plate or on the plate located under the chimney plate.

The inventive method also provides for a subdivision of the liquid withdrawn from the chimney plate, so that between 5 and 30 volume percent of this liquid is supplied directly to the plate located underneath, and the rest is supplied to the side heating device. For this purpose the chimney plate can be provided with an overflow weir, behind which a discharge cup for liquid withdrawl to the side heating device and a discharge shaft for the liquid withdrawal to the plate located underneath are arranged. The percentage distribution of the total weir length in these both partial regions corresponds respectively to the desired percentage distribution of the liquid quantity. By this feature, it is assured in a simple manner that during different total liquid quantities on the chimney plate, the desired percentage distribution of both liquid partial streams is maintained.

By the withdrawal of a partial quantity of liquid from the chimney plate to the plate located underneath the same, a washing effect is produced on this plate which retains the solvent far from the chimney plate and supplies the same to the lower part of the distillation column. Due to this reduction of the solvent concentration on the chimney plate, the boiling temperature of the liquid supplied into the side heating device is reduced and the heating device output is increased. In other words, a higher portion of the return flow supplied to the distillation column can be evaporated in the side heating device.

For the return of the vapor-liquid mixture discharged via the top from the heating device to the distillation column, two options are possible in accordance with the present invention.

In the first option, this mixture is fed again to the feed plate of the distillation column. The feed plate is here any plate on which the extract to be reconditioned is supplied into the distillation column. The utilization of this method option is advantageous when the distillation column must be supplied with a lot of heat. It is however here required that at least three normal plates be arranged between the feed plate and the chimney plate.

In accordance with the second oprtion, the vapor-liquid mixture from the side heating device is fed to the plate located underneath the chimney plate.

In both cases it is advantageous when the further supply of the vapor-liquid mixture into the distillation column is performed tangentially, since in this case the separation of the vapor and liquid components is improved.

A distillation column in accordance with the present invention is identified in the drawing as a whole with reference numeral 1. An extract coming from the preceding extraction stage is supplied through a conduit 2 into a central region of the column 1. The plate to which the supply of the extract is performed is identified as a feed plate 3. The distillative distillation of the extract is performed in a conventional manner in the distillation column 1, and the hydrocarbon material to be recovered is withdrawn through a conduit 4 from the distillation column 1 as a head product.

A partial quantity of the withdrawn hydrocarbon is supplied through a conduit 5 as a return flow to the upper part of the distillation column 1. The withdrawal of the solvent released from the hydrocarbon to be recovered is performed from the sump of the distillation column 1 through a conduit 6, through which the solvent can be supplied to its further utilization to the not shown extraction stage. The heating of the distillation column 1 can be performed in a known manner by one or several sump circulating heating devices 7, which are connected by a liquid circulation through conduits 8 and 9 with the sump of the distillation column 1.

The distillation column 1 in accordance with the present invention is also provided with a side heating device 10 which in the first place must serve for further evaporation of the return flow fed through the conduit 5 into the distillation column 1. It is to be understood that the side heating device 10 is provided with elements required for its heating, which are not shown in the drawings. The liquid withdrawal to the side heating device 10 is performed from a chimney plate 11 located above the feed plate 3. The chimney plate 11, as can be understood from its name has a chimney 12 as well as an overflow weir 13 in accordance with the present invention.

The liquid which flows to the chimney plate 11 from above downwardly and is collected there flows upon reaching the respective liquid level through the overflow weir 13 and flows into the discharge cup 14 located underneath and in a discharge passage 15. Further details of the flow withdrawal will be explained in connection with FIG. 2. The partial stream of the liquid which flows from the discharge cup 14 is supplied through a conduit 16 into the lower part of the side heating device 10, while the remaining partial stream of the liquid flows through the discharge passage 15 to the plate 17 located underneath the chimney plate 11.

The vapor-liquid mixture escaping via the top from the side heating device 10 can be further supplied either through the conduit 18 to the feed plate 3 or through the conduit 19 directly to the plate 17 located under the chimney plate 11 in the distillation column 1. Since there are here two alternatives which, however, cannot be utilized simultaneously, they are shown in the drawing by the conduit 18 which is illustrated in a broken line. When the further supply through the conduit 18 is performed, at least three plates must be arranged between the feed plate 3 and the chimney plate 11 as shown in the drawing.

Figure 2:
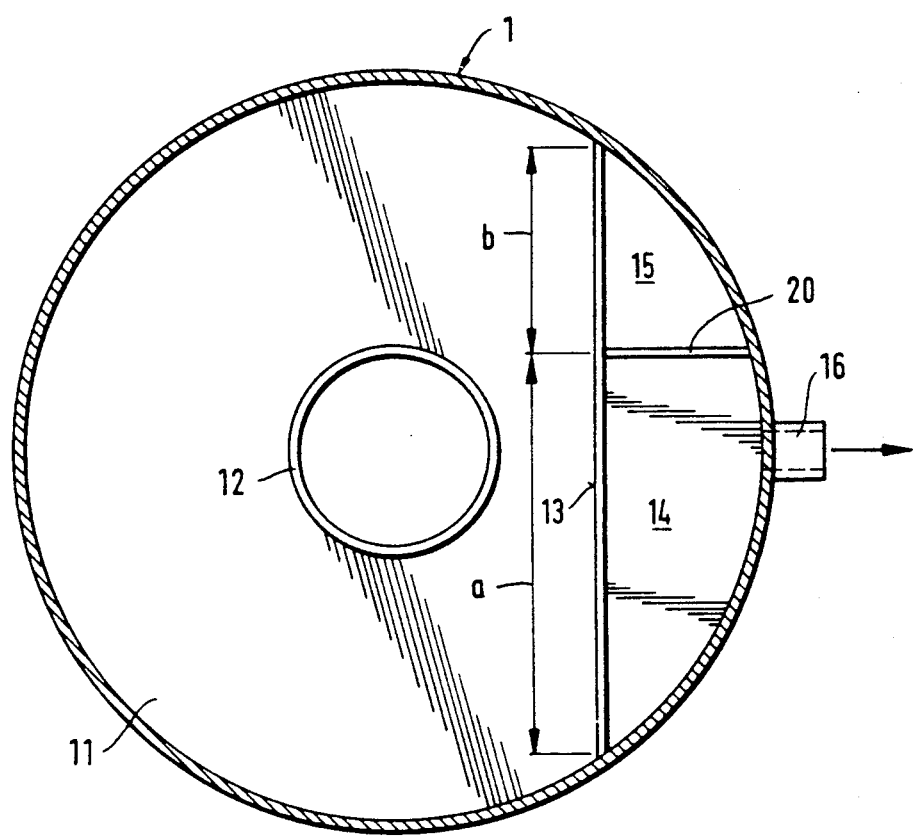
FIG. 2 is a plan view of a chimney plate of the distillation of the invention.

FIG. 2 shows a plan view of the chimney plate 11 with the associated chimney 12 and the overflow weir 13. The discharge cup 14 and the discharge passage 15 are located behind the overflow weir 13. They are separated from one another by a separating wall 20. The total length of the overflow weir is subdivided into the portions a and b so as to correspond to the desired distribution of both liquid streams. In other words, the portion b behind which the discharge passage 15 is located has a length of 5-30% of the total length of the overflow weir 13. As a result, between 5 and 30 volume percent of the liquid from the chimney plate 11 flows in the discharge passage 15 through this portion. The remaining fluid flows through the portion a in the discharge cup 14 and from there through the conduit 16 is withdrawn to the side heating device 10.

Since FIGS. 1 and 2 are only schematicaly showings, the size ratios represented in these Figures do not correspond to the size ratios which exist in the practice. It is to be understood that the distillation column 1, in contrast to the showing in FIG. 1 can have further plates in its upper and lower parts. They can be formed as separating plates of a conventional type. Moreover, it is believed to be understood that in practice this column is provided with the required measuring and regulating devices for controlling its operation.

Figure 3:
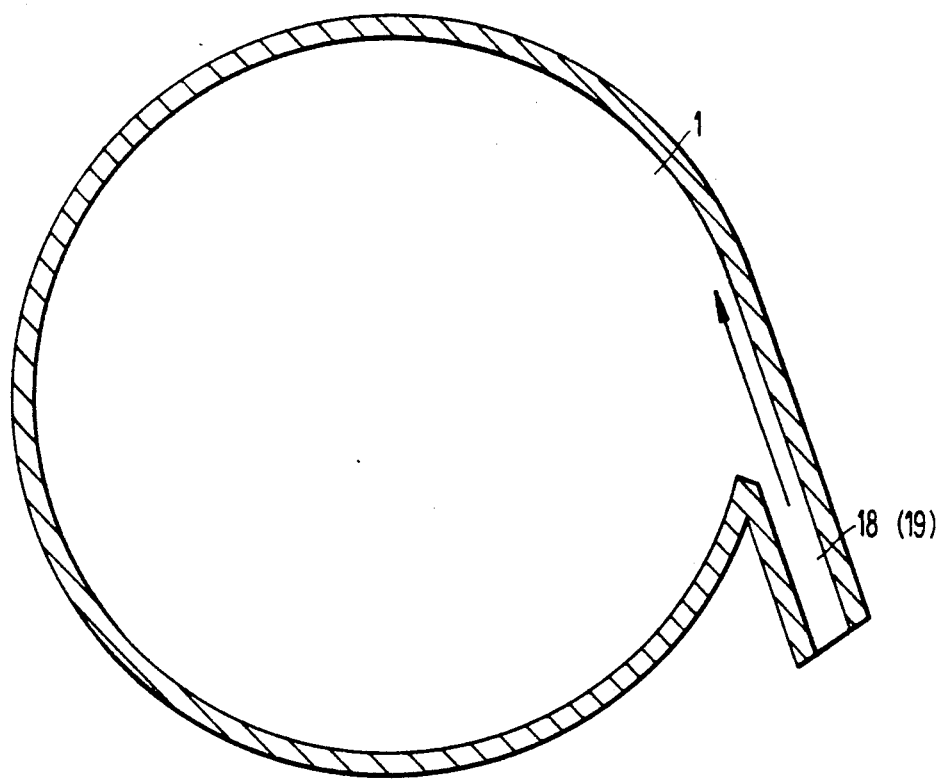
FIG. 3 shows a section of the distillation column of the invention with a tangential return of a vapor-liquid mixture from a side heating device to the column.

FIG. 3 shows that the vapor-liquid mixture can be returned from the side heating device 10 tangentially to the distillation column 1.

While the invention has been illustrated and described as embodied in a method of and arrangement for optimizing the operation of a distillation column provided with a side heating device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A method of optimizing the operation of a distillation column with a side heating device for reconditioning of extracts which are received during the extraction of hydrocarbon-containing initial products with N-substituted morpholines whose substituents have not more than seven carbon atoms as selective solvents, comprising the steps of feeding an extract as a liquid to a distillation column provided with a feed plate; removing hydrocarbons and solvent recovered from the extract from the distillation column; withdrawing the extract as a side stream from the distillation column to a side heating device through chimney plate arranged above the feed plate of the distillation column, so that between 5 and 30 volume percent of the extract supplied to the chimney plate is not withdrawn to the side heating device but instead is supplied directly to a plate located under neath the chimney plate; returning a vapor-liquid mixture which has escaped through a top of the side heating device back to the distillation column; and feeding the returned vapor-liquid mixture either to the feed plate or to the plate located underneath the chimney plate.

2. A method as defined in claim 1, wherein the vapor-liquid mixture is returned from the side heating device to the distillation column tangentially to the distillation column.

3. A method as defined in claim 1, wherein the vapor-liquid mixture from the side heating device is returned to the feed plate of the distillation column and is performed so that at least three plates are arranged between the feed plate and the chimney plate.

* * * * *